US011538562B1

(12) United States Patent
Trent et al.

(10) Patent No.: US 11,538,562 B1
(45) Date of Patent: Dec. 27, 2022

(54) TRANSMISSION OF MEDICAL INFORMATION IN DISRUPTED COMMUNICATION NETWORKS

(71) Applicant: ARCHITECTURE TECHNOLOGY CORPORATION, Eden Prairie, MN (US)

(72) Inventors: Barry Trent, Eden Prairie, MN (US); Jafar Al-Gharaibeh, Eden Prairie, MN (US)

(73) Assignee: ARCHITECTURE TECHNOLOGY CORPORATION, Eden Prairie, MN (US)

( * ) Notice: Subject to any disclaimer, the term of this patent is extended or adjusted under 35 U.S.C. 154(b) by 402 days.

(21) Appl. No.: 16/781,850

(22) Filed: Feb. 4, 2020

(51) Int. Cl.
*H04L 67/60* (2022.01)
*H04W 4/80* (2018.01)
*G16H 10/60* (2018.01)
*H04L 67/141* (2022.01)

(52) U.S. Cl.
CPC ........... *G16H 10/60* (2018.01); *H04L 67/141* (2013.01); *H04L 67/60* (2022.05); *H04W 4/80* (2018.02)

(58) Field of Classification Search
None
See application file for complete search history.

(56) References Cited

U.S. PATENT DOCUMENTS

| 5,115,433 A | 5/1992 | Baran et al. |
| 6,658,481 B1 | 12/2003 | Basso et al. |
| 6,985,476 B1 | 1/2006 | Elliott et al. |
| 7,317,733 B1 | 1/2008 | Olsson et al. |
| 7,562,028 B1 * | 7/2009 | Donner ............ G06Q 30/0603 705/5 |
| 7,627,629 B1 | 12/2009 | Wu et al. |
| 8,627,449 B2 * | 1/2014 | Parla ....................... H04L 63/08 709/227 |

(Continued)

FOREIGN PATENT DOCUMENTS

WO   WO-2019007491 A1 *   1/2019   ........... H04L 1/0045

OTHER PUBLICATIONS

"Internet Protocol, DARPA Internet Program Protocol Specification", Sep. 1981, 97 pages, USA.

(Continued)

*Primary Examiner* — Uzma Alam
(74) *Attorney, Agent, or Firm* — Foley & Lardner LLP

(57) ABSTRACT

Described herein are methods and systems to send/receive medical data from one or more electronic devices to a secondary medical unit in delayed, intermittently-connected, low-bandwidth (DIL) environments. An application executing on the electronic devices may, in response to detecting a disruption within a communication network, execute an offline communication protocol to transmit medical data among a predetermined number of other electronic devices, wherein the offline communication protocol does not use the communication network. The application may then receive a request from a server of the secondary medical unit to transmit at least a part of the medical data. In response to authenticating the request, the application then transmits the medical data using an online communication protocol that uses the communication network or using an offline communication protocol.

20 Claims, 5 Drawing Sheets

(56) References Cited

U.S. PATENT DOCUMENTS

| | | | |
|---|---|---|---|
| 8,886,195 B2* | 11/2014 | Srinivasan | H04W 88/06 |
| | | | 455/445 |
| 9,191,377 B2 | 11/2015 | Charan et al. | |
| 9,225,637 B2 | 12/2015 | Ramanujan et al. | |
| 9,489,291 B2 | 11/2016 | Moore et al. | |
| 9,742,664 B2* | 8/2017 | Carson | H04L 45/245 |
| 10,075,548 B2* | 9/2018 | Kim | H04W 12/04 |
| 10,326,617 B2 | 6/2019 | Al-Gharaibeh et al. | |
| 10,587,509 B2 | 3/2020 | Ramanujan et al. | |
| 2001/0027484 A1 | 10/2001 | Nishi | |
| 2002/0010633 A1* | 1/2002 | Brotherston | B64D 11/0015 |
| | | | 705/26.8 |
| 2002/0184055 A1* | 12/2002 | Naghavi | G16H 40/63 |
| | | | 705/2 |
| 2003/0046390 A1 | 3/2003 | Ball et al. | |
| 2003/0112808 A1 | 6/2003 | Solomon | |
| 2003/0125028 A1 | 7/2003 | Reynolds | |
| 2004/0032873 A1 | 2/2004 | Basso et al. | |
| 2006/0187858 A1 | 8/2006 | Kenichi et al. | |
| 2008/0049641 A1 | 2/2008 | Edwards et al. | |
| 2008/0167025 A1* | 7/2008 | Williamson | H04L 67/52 |
| | | | 455/418 |
| 2009/0063187 A1* | 3/2009 | Johnson | H04L 67/52 |
| | | | 705/2 |
| 2009/0157882 A1* | 6/2009 | Kashyap | H04L 67/1001 |
| | | | 709/227 |
| 2010/0061231 A1 | 3/2010 | Harmatos et al. | |
| 2010/0142395 A1 | 6/2010 | Yasuie et al. | |
| 2010/0235514 A1 | 9/2010 | Beachem | |
| 2010/0268935 A1 | 10/2010 | Rodgers et al. | |
| 2010/0329270 A1 | 12/2010 | Asati et al. | |
| 2011/0075552 A1 | 3/2011 | Mitsumori | |
| 2011/0125921 A1 | 5/2011 | Karenos et al. | |
| 2011/0134906 A1* | 6/2011 | Garudadri | H04W 52/0209 |
| | | | 370/350 |
| 2011/0211463 A1 | 9/2011 | Matityahu et al. | |
| 2012/0039202 A1* | 2/2012 | Song | H04W 72/00 |
| | | | 370/252 |
| 2012/0063316 A1 | 3/2012 | Ghanwani et al. | |
| 2012/0082073 A1 | 4/2012 | Andreasen et al. | |
| 2012/0106566 A1 | 5/2012 | Zarrabi et al. | |
| 2012/0327811 A1 | 12/2012 | Nozaki | |
| 2013/0215810 A1 | 8/2013 | Wang et al. | |
| 2014/0105033 A1 | 4/2014 | Vasseur et al. | |
| 2014/0348024 A1* | 11/2014 | Mishra | H04W 36/30 |
| | | | 370/254 |
| 2014/0363152 A1 | 12/2014 | Hironaka et al. | |
| 2014/0369489 A1 | 12/2014 | Ermann et al. | |
| 2015/0010002 A1 | 1/2015 | Duda et al. | |
| 2015/0124586 A1* | 5/2015 | Pani | H04L 61/5007 |
| | | | 370/219 |
| 2015/0149764 A1 | 5/2015 | Charan et al. | |
| 2015/0154104 A1 | 6/2015 | Moore et al. | |
| 2015/0188991 A1* | 7/2015 | Huang | H04L 67/10 |
| | | | 709/217 |
| 2015/0215210 A1 | 7/2015 | Shen et al. | |
| 2015/0257081 A1 | 9/2015 | Ramanujan et al. | |
| 2015/0264626 A1* | 9/2015 | Perdomo | H04L 67/52 |
| | | | 370/216 |
| 2015/0312363 A1* | 10/2015 | Robinson | H04L 67/56 |
| | | | 709/219 |
| 2015/0318911 A1 | 11/2015 | Samios | |
| 2016/0147944 A1* | 5/2016 | Douglass | G06F 21/31 |
| | | | 705/51 |
| 2016/0255667 A1 | 9/2016 | Schwartz | |
| 2017/0111784 A1* | 4/2017 | Vanover | H04W 76/14 |
| 2017/0155580 A1 | 6/2017 | Ramanujan et al. | |
| 2017/0163525 A1* | 6/2017 | Fedor | H04W 28/0236 |
| 2017/0199972 A1* | 7/2017 | Hussam | G16H 10/60 |
| 2017/0302478 A1 | 10/2017 | Al-Gharaibeh et al. | |
| 2018/0004908 A1* | 1/2018 | Barrus | G16H 40/67 |
| 2018/0199259 A1* | 7/2018 | Choi | H04W 40/22 |
| 2018/0255591 A1* | 9/2018 | Valicherla | H04L 12/4641 |
| 2018/0349406 A1* | 12/2018 | Shortlidge | G16H 10/60 |
| 2019/0104202 A1* | 4/2019 | Reynolds | H04L 41/0853 |
| 2021/0281412 A1* | 9/2021 | Khoury | H04L 63/123 |
| 2022/0076506 A1* | 3/2022 | de Matos | G07C 1/12 |
| 2022/0139510 A1* | 5/2022 | Romanychev | H04B 5/0031 |
| | | | 705/2 |

OTHER PUBLICATIONS

"OSPF Design Guide", Cisco, pp. 1-55, 2005.
"Tactical Targeting Network Technology, Dynamic, Robust Waveform enabling NetCentric Communications for Today's Warfighter", Rockwell Collins, 19 pages, 2009, USA.
"Talk II-SINCGARS, Multiservice Communications Procedures for the Single-Channel Ground and Airborne Radio System", Marine Corps, 78 pages, May 1996.
"Transmission Control Protocol, DARPA Internet Program Protocol Specification", Sep. 1981, 89 pages, USA.
"Wideband Gapfiller System", GlobalSecurity.org, http://www.globalsecurity.org/space/systems/wgs.htm, pp. 1-5, Oct. 4, 2016.
Spagnolo, Phillip A., et al., "Boeing Quagga Software", The Boeing Company, 3 pages, 2006.
Architecture Technology Corporation, Topic: DHA191-005, Proposal # H191-005-0047.
Berry, et al., "PPP over Ethernet (PPPoE) Extensions for Credit Flow and Link Metrics", Internet Engineering Task Force, Feb. 2010, 24 pages, USA.
Burbank, Jack L. et al. "Key Challenges of Military Tactical Networking and the Elusive Promise of MANET Technology," IEEE Communications Magazine, Nov. 2006, 7 pages.
Chau, Chi-Kin et al. "IDRM: Inter-Domain Routing Protocol for Mobile Ad Hoc Networks," Technical Report No. 708, 2008. UCAM-CL-TR-708, ISSN 1476-2986 University of Cambridge, Jan. 2008, pp. 1-24.
Lee, Seung-Hoon, "Inter MR: Inter-MANET Routing in Heterogeneous MANETs," Proceedings of MASS' 2010, Nov. 2010, 10 pages.
Macker, Joseph P. et al. "Heterogeneous Architecture Support for Wireless Network Dynamics and Mobility," Naval Research Laboratory, NRL/MR/5520-00-8513. Dec. 29, 2000, 31 pages.
Pei, Dan et al. "BGP-RCN: Improving BGP Convergence Through Root Cause Notification," Computer Networks. Sep. 28, 2004, 20 pages.
Perkins, C., "Minimal Encapsulation within IP", Internet Engineering Task Force, Oct. 1996, pp. 1-6, USA.
Pizzi, Steven V. "A Routing Architecture for the Airborne Network" MILCOM Paper Tracking No. 248, Version 5.40. 2007 The MITRE Corporation. May 21, 2007, pp. 1-7.
Rekhter, Y. et al. "A Border Gateway Protocol 4 (BGP-4)" IETF RFC 1771, Mar. 1995, [online] [retrieved on Jul. 16, 2014], retrieved from the internet 57 pages.
Rekhter, Y. et al. "Application of the Border Gateway Protocol in the Internet" IETF RFC 1772. Mar. 1995, 19 pages.

* cited by examiner

TRANSMISSION OF MEDICAL INFORMATION IN DISRUPTED COMMUNICATION NETWORKS

TECHNICAL FIELD

The present disclosure relates generally to communication among electronic devices in disrupted networks.

BACKGROUND

To replace error-prone, hand-written medical assessments, many first responders utilize software technology to input/revise their medical assessments. For instance, first responders (e.g., paramedics) may utilize a user interface provided by these medical software applications to input their findings and assessments into an electronic device. The medical software applications then synchronize the data with a central server/database providing a unified medical record for patients. This unified and central medical record could be utilized by other medical professionals (e.g., doctors) or medical evacuation units.

However, since the implementation of these medical software applications, many technical shortcomings have been identified. Conventional medical software uses wired and wireless communication technology (e.g., Wi-Fi, cellular, and USB connectivity options) to synchronize/transfer the inputted data. However, these conventional communication protocols may not always be available. For instance, military first responders (e.g., medics) operate in a severely disadvantaged communication environments. Part of the medics' communication disadvantage is due to the chaotic, noisy, interference-filled forward-deployed tactical environment in which they operate. A larger part of the problem is that the operational requirements of the forward-deployed tactical environment are onerous, in that the Wi-Fi and cellular radio-based capabilities of the mobile devices may be required to be completely disabled. The combination of these two factors means that medics confront a delayed, intermittently-connected, low-bandwidth (DIL) environment in which they may have little or no connectivity at the critical times when they are tasked with stabilizing, treating, and evacuating injured personnel. There may be no internet or IP-enabled infrastructure available and, at best, connectivity may be time-varying, with an unpredictable network topology.

Therefore, conventional software solutions cannot provide effective assistance to first responders in warzone, catastrophes, or in DIL environments.

SUMMARY

For the aforementioned reasons, there is a desire for software-based IP integration routers/applications that allow for peer-to-peer (P2P) and client/server exchange of critical medical data among the group of medics in DIL environments. What is desired is an effective hand-off of the medical data, in its entirety, to other medical professionals (e.g., secondary medical personnel, such as the evacuation personnel who later arrive on scene). The methods and systems described herein provide a flexible way to share medical data in the face of intermittent or inconsistent network access. When network connectivity is completely unavailable, the methods and systems described herein allow a system that will buffer and delay data transfers until communication is available in some form, incorporating advanced disruption tolerant networking (DTN) technology where appropriate. The methods and systems described herein are agnostic to the particular link-layer communications technologies employed, and will include at least one option to share data, which can operate effectively without any radio-frequency emissions.

In an embodiment, a computer system for enabling communication in disrupted communication networks, the computer system comprising a database associated with a medical evacuation vehicle and configured to store medical data associated with one or more users from at least one electronic device; a plurality of electronic devices, each electronic device having a first software application configured to receive medical data associated with one or more users; a second software application configured to enable communication with at least one other electronic device within the plurality of electronic devices and the database, the second software application further configured to in response to detecting a disruption within a communication network among the plurality of electric devices, executing an offline communication protocol to transmit medical data associated with the first software application to a predetermined number of other electronic devices within the plurality of electronic devices, wherein the offline communication protocol does not use the communication network; receive a request from a server associated with the database to transmit at least a part of the medical data associated with at least one user; in response to authenticating the request, transmit the medical data associated with the first software application of the predetermined number of other electronic devices within the plurality of electronic devices to the database.

In another embodiment, a computer-implemented method for enabling communication in disrupted communication networks, the method comprising in response to detecting a disruption within a communication network among the plurality of electric devices, executing, by a first application executing on at least one electronic device, an offline communication protocol to transmit medical data to a predetermined number of other electronic devices within the plurality of electronic devices, wherein the offline communication protocol does not use the communication network, and wherein the medical data is inputted by a user operating at least one electronic device via a second application executing on the plurality of electronic devices; receive, by the application, a request from a server associated with a database of a medical evacuation vehicle to transmit at least a part of the medical data associated with at least one user; in response to authenticating the request, transmit the medical data associated with the first software application of the predetermined number of other electronic devices within the plurality of electronic devices to the database; and in response to authenticating the request, transmitting, by the application, the medical data associated with the first software application of the predetermined number of other electronic devices within the plurality of electronic devices to the database.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1A:
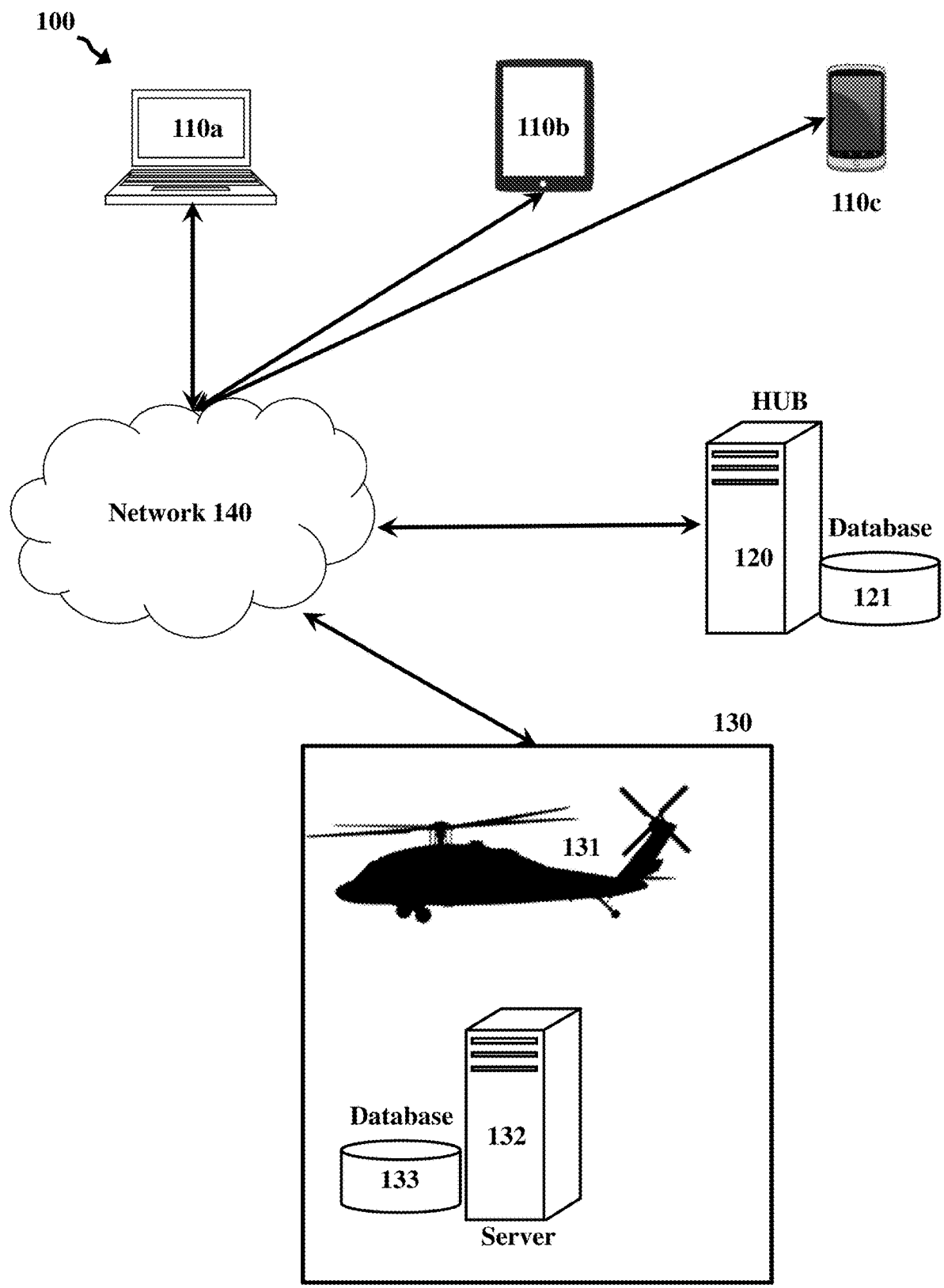
FIG. 1A illustrates components of a computer system for sharing medical data in a delayed, intermittently-connected, low-bandwidth (DIL) environment, according to an embodiment.

Reference will now be made to the illustrative embodiments illustrated in the drawings, and specific language will be used herein to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Figure 1B:
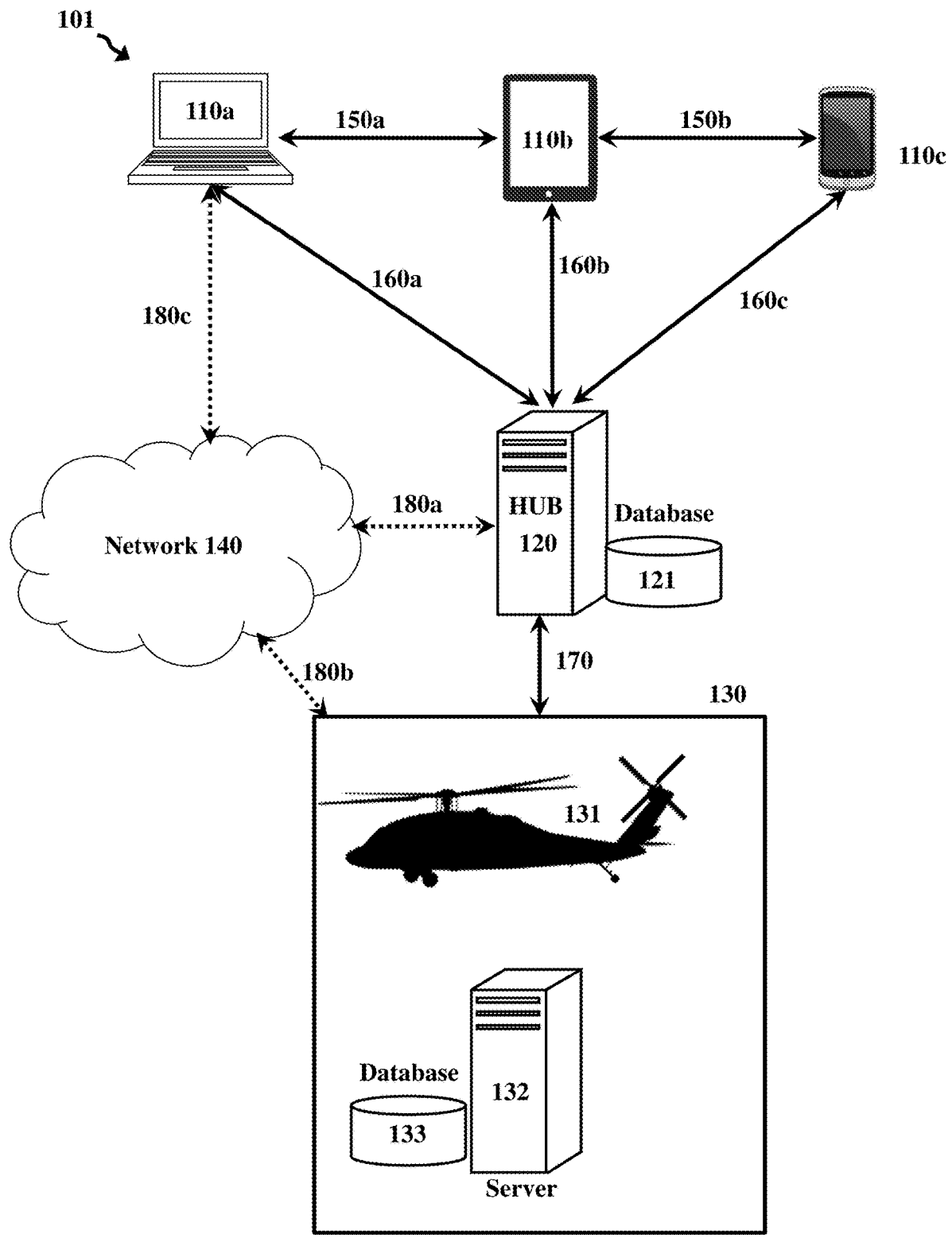
FIG. 1B illustrates components of a computer system for sharing medical data in a DIL environment, according to an embodiment.
Figure 1C:
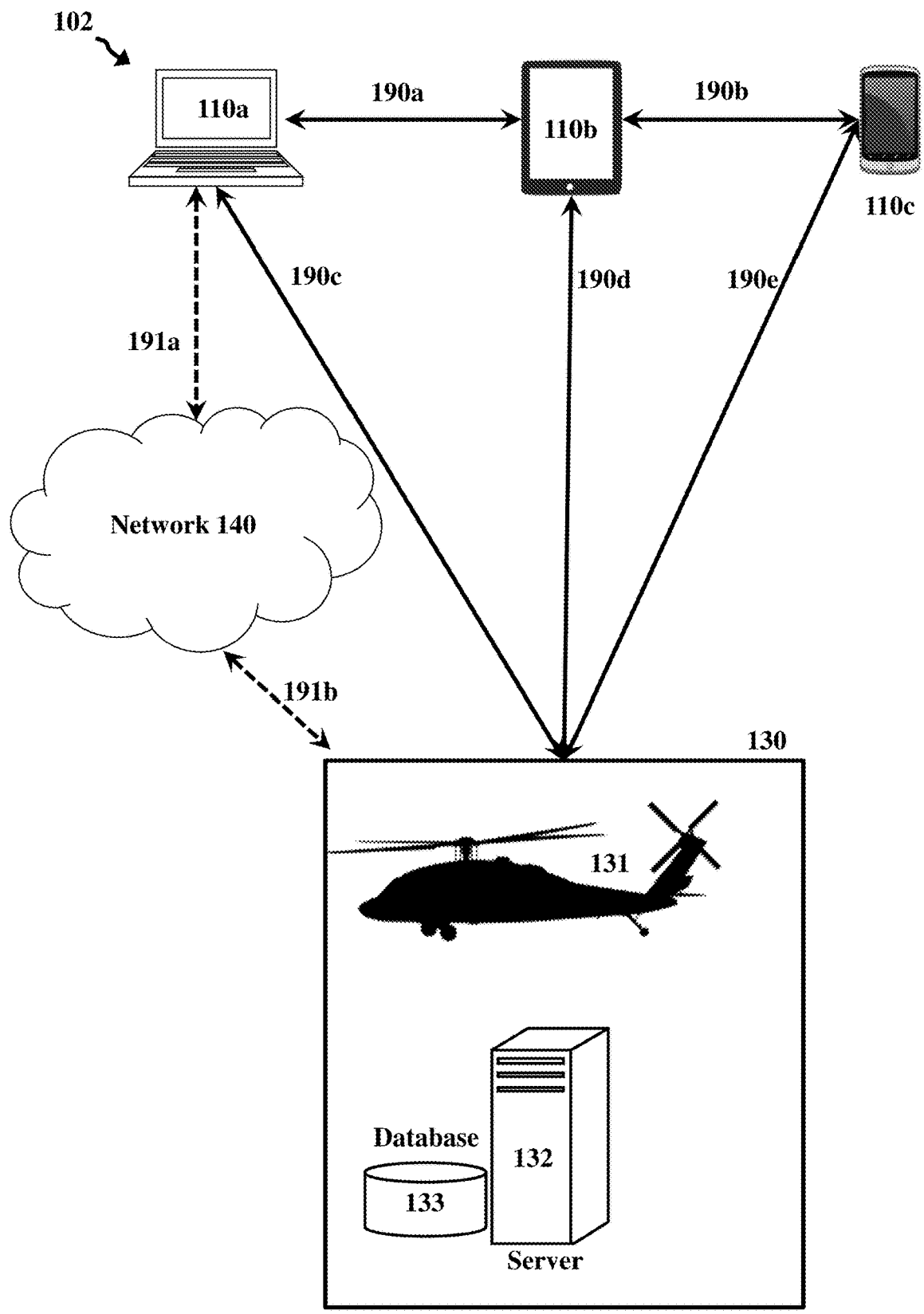
FIG. 1C illustrates components of a computer system for sharing medical data in a DIL environment, according to an embodiment.

FIG. 1A-1C illustrates components of a computer system for sharing medical data in a DIL environment, according to an embodiment. The system 100 may include electronic user devices 110a-c (collectively electronic user devices 110), hub 120, database 121, and a secondary medical unit 130 having a vehicle 131, server 132, and database 133. In some configurations, the above-described features are connected to each other through a network 140. The examples of the network 140 may include, but are not limited to, private or public LAN, WLAN, MAN, WAN, and the Internet. The network 140 may include both wired and wireless communications according to one or more standards and/or via one or more transport mediums.

The communication over the network 140 may be performed in accordance with various communication protocols such as transmission control protocol and Internet protocol (TCP/IP), user datagram protocol (UDP), and IEEE communication protocols. In one example, the network 140 may include wireless communications according to Bluetooth specification sets, or another standard or proprietary wireless communication protocol. In another example, the network 140 may also include communications over a cellular network, including, e.g., a global system for mobile communications (GSM), code division multiple access (CDMA), and enhanced data for global evolution (EDGE) network.

The electronic user devices 110 may refer to any portable or non-portable device, such as a desktop computer, laptop computer, tablet computer, smart phone, smart watch, gaming console, personal digital assistant, and the like. The electronic user devices 110 may be any computer with a processor/microcontroller and/or any other electronic component that performs one or more operations according to one or more programming instructions. The electronic user devices 110 may be capable of communicating with other electronic devices, the secondary medical unit 130, and/or the hub 120 through the network 140 using wired or wireless communication capabilities. In some other embodiments, such as in DIL environments, the electronic user devices 110 may connect to other electronic devices using other means that will be described below.

In operation, first responders may use the electronic user devices 110 to access one or more software applications (e.g., web applications) installed on the electronic user devices 110 to enter their medical assessment and input medical information. In addition to executing the medical software applications, also referred hereto as the first software application, the electronic user devices may also execute a secondary software application that enables the electronic user device to communicate with each other, the hub 120, and/or with the secondary medical unit 130. The secondary software application may be an application, software, or an executable file installed onto each electronic user device 110a-c. The secondary software application may be executing in the background of the electronic user devices 110. As a result, the secondary software application may not obfuscate the display of the electronic user devices 110 or interfere with the first responder's workflow. In some configurations, one application may act as the first and the second applications.

The electronic user devices 110 may be equipped with hardware, modules, and software that enables wireless and wired communication with other devices described herein. For instance, each electronic device may be equipped with near field communication (NFC) or contactless communication protocols that enable the electronic user devices 110 to electrically transmit and receive data from another electronic device (e.g., another electronic user device 110, the hub 120, and/or the secondary medical unit 130). As will be described below, the secondary application may use a variety of online and offline communication protocols to transmit data within various electronic devices/features described herein.

The hub 120 may be any computing device comprising a processor and non-transitory machine-readable storage capable of executing the various tasks and processes described herein. Non-limiting examples of such computing devices may include workstation computers, laptop computers, server computers, laptop computers, and the like. While the system 100 includes a single hub 120, one having skill in the art would appreciate that in some embodiment, the hub 120 may include any number of computing devices operating in a distributed computing environment. The hub 120 may also include a data repository module (e.g., a database 121) configured to store data. The hub 120 may be an intelligent communication hub, as described in U.S. Pat. No. 10,326,617, which is incorporated herein in its entirety.

The database 121 may be hosted on any number of computing devices comprising a non-transitory machine-readable storage medium and capable of performing the various tasks described herein. As shown in FIG. 1A-1C, the hub 120 may be accessed by one or more electronic user devices 110 and/or any electronic device of the secondary medical unit 130. The database 121 may be hosted on the same physical computing device functioning as the hub 120. In some embodiments, the database 121 may have a logical construct of data files that are stored in non-transitory machine-readable storage media, such as a hard disk or memory, controlled by software modules of a database program (e.g., SQL), and a related database management system (DBMS) that executes the code modules (e.g., SQL scripts) for various data queries and other management functions generated by the hub 120.

The secondary medical unit 130 may represent a second group of medical professionals (e.g., medical evacuation unit) that may need the medical data from the first responders (e.g., electronic user devices 110). The secondary medical unit 130 may include a vehicle 131 (e.g., boat, automobile, ambulance, or medical evacuation helicopter). The vehicle 131 may include a server 132 and a database 133 used by the secondary medical professionals to receive medical data from the electronic user devices 110.

The server 132 may be any computing device comprising a processor and non-transitory machine-readable storage capable of executing the various tasks and processes described herein. Non-limiting examples of such computing devices may include workstation computers, laptop computers, server computers, laptop computers, and the like. While the system 100 includes a single server 132, one having skill in the art would appreciate that in some embodiment, the server 132 may include any number of computing devices operating in a distributed computing environment. The server 132 may also include a data repository module (e.g., a database 133) configured to store data.

The database 133 may be capable of storing user profiles and various web/electronic documents associated with various projects. The server 132 may query and retrieve various documents from the database 133. The database 133 may be in communication with a processor of the server 132 and/or the electronic user devices 110, where the processor is capable of executing the various commands of the system 100. In some embodiments, the database 133 may be part of the server 132 or the electronic user devices 110. In some embodiments, the database 133 may be a separate computing feature/component in communication with the server 132. In some configurations, the database 133 may be a part of the server 132.

As will be described below, the methods and systems described herein transmit data from the electronic user devices 110 to the secondary medical unit 130 using various methods. For instance, as illustrated in the system 101 in FIG. 1B, the secondary application may enable offline communication with the secondary medical unit 130 using the hub 120. Additionally or alternatively, as illustrated in the system 102 in FIG. 1C, the secondary application may enable offline communication between the electronic user devices 110 and the secondary medical unit 130.

In a non-limiting example, as depicted in FIG. 1B (e.g., system 101), when the application executing on the electronic user devices 110 identifies that the network 140 is no longer available (e.g., DIL environment), the application enables offline communication between each electronic user device 110a-c and the hub 120 and its database 121. For instance, the application enables (e.g., activates) various offline communication protocols and allows the electronic user devices 110 to communicate with each other (e.g., communication 150a and 150b).

The offline communication may be any offline communication protocol described herein. For instance, medics using the electronic device 110a may use NFC communication protocols to communicate with the electronic device 110b (e.g., communication 150a). In a non-limiting example, an operator of the electronic device 110a may "bump" the electronic device 110a with the electronic device 110b (e.g., bring the electronic devices within a predetermined physical proximity to enable the NFC communication to be executed).

When the application executing on both electronic devices identify that the electronic devices are within a predetermined physical proximity, the applications transmit medical data stored locally on the electronic device 110a to the electronic device 110b and vice versa. In some embodiments, each time two electronic devices connect or communicate, the application may store all the medical data from each electronic device onto both electronic devices. In this way, all the electronic devices may receive (directly or indirectly) and store the medical data from all the electronic devices. For instance, the electronic device 110c may receive the medical data generated by the electronic device 110a via the offline communication 150b with the electronic device 110b.

The application may then enables offline communication between the electronic devices and the hub 120 (e.g., communication 160a-160c). Because each electronic device within the electronic user devices 110 possesses (e.g., locally stores) all medical data (e.g., medical data for all other electronic user devices 110), the secondary medical unit may only need to communicate with the hub 120 one time to gather all the medical data (e.g., communication 170).

In some embodiments, when the application determines that the secondary medical unit 130 is within a predetermined proximity (e.g., 50 feet), the application may enable online communication protocols where the hub 120 can utilize the communication network 140 to communicate with the server 132 (e.g., online communication 180a-b). The application may also enable online communication between one or more electronic devices 110 with the secondary medical unit 130 (e.g., online communication 180c and 180b). In this way, the secondary medical unit 130 may only need to communicate with one device (only one time) to receive all the medical data. These online communication protocols may be optional and may not be performed each time. Consequently, they are depicted in dashed lines. These online communications may also be temporary. For instance, the application may only enable these online communications for a predetermined time period (e.g., 5 minutes).

In a secondary configuration, as depicted in FIG. 1C (e.g., system 102), the application may only enable communication between the electronic user devices 110 and the secondary medical unit 130. As described above, the application may enable offline communication between the electronic user devices 110 and allow each electronic device to share its medical data with others (e.g., offline communication 190a and 190b). When the application determines that the secondary medical unit 130 is within a predetermined proximity, the application then enables offline communication between one or more electronic user devices 110 and the secondary medical unit 130 (e.g., electronic communication 190c-d. Additionally or alternatively, the application may also allow temporary online communication between one or more electronic user devices 110 and the secondary medical unit 130 (e.g., online communications 191a-b).

Figure 2:
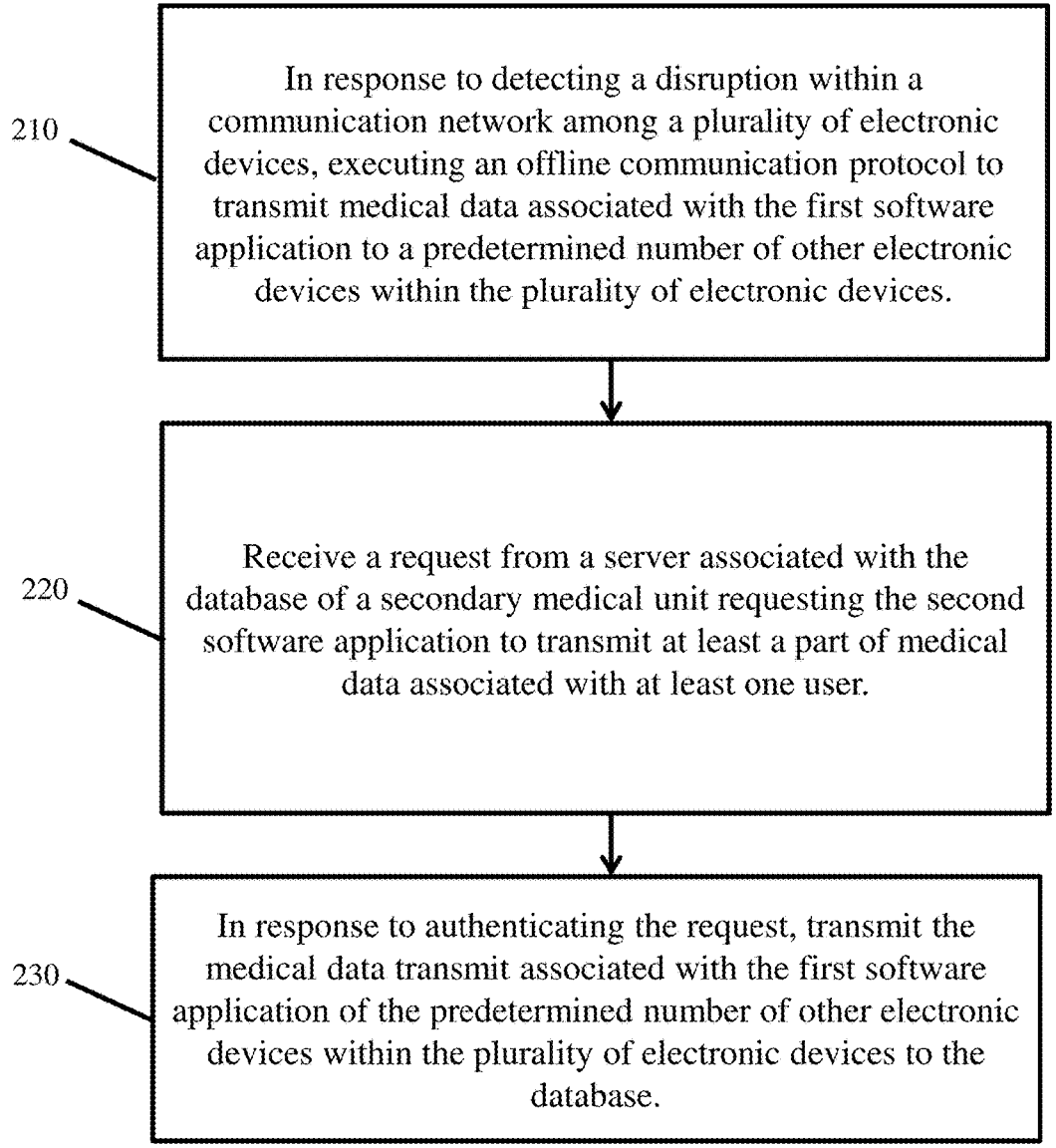
FIG. 2 is a flow diagram of an illustrative process/method for sharing medical data in a DIL environment, according to an embodiment.

FIG. 2 is a flow diagram of an illustrative process/method for sharing medical data in a DIL environment, according to an embodiment. However, other embodiments may comprise additional or alternative execution steps, or may omit one or more steps altogether. Some embodiments may perform certain execution steps in a different order. One or more steps may also be performed simultaneously or near-simultaneously with one another.

In addition, the method 200 is described as being executed by an application installed onto the electronic devices of first responders. However, in some embodiments, various steps may be executed by any number of computing devices operating in a distributed computing environment. In some configurations, a computer executing one or more steps may be programmed to execute various other features, where such computer does not need to be operating strictly as the analytics server described herein. The method 200 describes embodiments where an application executing on the first responders' electronic devices can enable communication with secondary medical unit computer systems in DIL environments.

At step 210, an application executing on one or more electronic devices may, in response to detecting a disruption within a communication network among a plurality of electronic devices, executing an offline communication protocol to transmit medical data associated with the first software application to a predetermined number of other electronic devices within the plurality of electronic devices.

As described above, each electronic device may be equipped with at least two applications. The first application may be configured to receive medical data from the first responders. The first application may execute various software codes and may display various graphical user interfaces having various input fields to collect data inputted by the first responders operating the electronic devices. The data generated via the first responders' interactions with the first application may be stored locally within each electronic device.

The second application may be enabled to transmit the data stored onto each electronic device (e.g., data generated via the first responders' interactions with the first application) to other medic device's and/or a secondary medical unit's computing system. In the method 200, the "application" refers to the secondary application that enables the medical data to be transmitted to other electronic devices in DIL environments.

The application may first identify a disruption in the communication network connecting one or more electronic devices. The application may periodically monitor various communication networks used by the electronic devices to transmit/receive (e.g., download and/or upload) data. The application may use a variety of methods to identify the network(s) disruption where the network used by the electronic devices may be unable to support one or more desired communication protocols.

In some embodiments, such as war zones, the application may receive an instruction to communicate sensitive medical data without using conventional communication protocols or the communication network. In some embodiments, the application may identify that the network is not suitable to be utilized by the electronic devices. For instance, the application may receive a request to stop utilizing the network due to security concerns. In a non-limiting example, the application may be configured to synchronize medical data generated by electronic devices operated by medics at a war zone. The application may receive a notification that the network is no longer secure and the users may not transmit data using the network. The application may identify (or receive a notification from a different device/server) that cyber attackers have gained inappropriate access to the communication network. As a result, the application may then use the methods and systems described herein to transmit the medical data (e.g., data generated by the medics using the first application) to a secondary medical unit.

As used herein "offline communication" refers to any communication without using the communication network. In some configurations, the application may use the communication network. However, the application may use various methods (described below) to ensure data security. Furthermore, "online communication" refers to any communication using the communication network. Methods and systems described herein allow the electronic devices to communicate data using a combination of offline and online communication methods. These methods and systems allow the data to remain secure. These methods and systems also prevent identification data associated with the electronic devices (e.g., digital signature) from being compromised. When the application identifies a network disruption, the application enables the electronic devices to execute offline communication protocols.

Offline Communication Protocols

In some embodiments, the application may utilize a visual data transfer method to send/receive data among electronic devices and/or a central hub. In one example, the application may generate an encrypted media element based on the medical data associated with one or more users. The application may then display the encrypted media element on a first electronic device. A second electronic device may then receive the medical data when the second electronic device receives an image of the encrypted media element.

In a non-limiting example, a first medic operating a first mobile device may input medical data associated with a soldier into input fields displayed on the first mobile device. When the first medic desires to transfer the medical data to a second medic operating a second mobile device, the first medic may instruct the application to generate an encrypted media element corresponding to the soldier's medical data. The application may then display the encrypted media element on the first mobile device. In order to transfer the medical data to the second mobile device, the second medic may take a picture of the encrypted media element displayed on the first mobile device. The application, executing on the second mobile device, may then decrypt the encrypted media element and store the medical data onto the second mobile device.

An example of an encrypted media element may be a quick response code (QR code). A QR Code is a type of encrypted matrix barcode (two-dimensional or three-dimensional barcodes). A QR is a machine-readable optical label that may contain data associated with the user or other data. The application may generate the QR Code based upon one or more data fields of the medical data inputted by a user, device identifier associated with the electronic device, and the like. A QR code may consist of black squares arranged in a square grid on a white background, which can be read by an imaging device such as a camera, and processed using Reed—Solomon error correction until the image can be appropriately interpreted. The required data may be then extracted from patterns that are present in both horizontal and vertical components of the image.

In some embodiments, the media element is not encrypted but is only unique (e.g., unique per user or data). For example, the application may generate a unique machine readable media element based on above-mentioned information, which is only valid for a one-time data transfer.

In some embodiments, the application may utilize a low-overhead routing method to send/receive data among electronic devices and/or a central hub. Low-overhead routing, as used herein, may refer to sending/receiving data using a hybrid router using an autonomous Internet Protocol (IP)-based network integration solution that provides end-to-end sensor-to-shooter connectivity across a heterogeneous tactical network. This network may consist of IP sub-networks of various types such as tactical targeting network technology (TTNT), mini-CDL (common data link), free space optics communications (FSOC), quint networking technology (QNT), and joint capability for airborne networking (JCAN). These integrated networks may provide improved tactical communications and situational awareness. As used herein, network integration may refer to the convergence of many IP devices (e.g., wired, wireless, radio, and optical devices) each forming IP subnets into a single IP network. Each of the device subnets may be IP capable on their own, but may not be able to integrate seamlessly and automatically with others.

In an embodiment, a single routable network may have a plurality of heterogeneous subnetworks having different network parameters and an integration router containing a plurality of network interfaces, each of the plurality of network interfaces configured to be connected to a different one of the plurality of heterogeneous subnetworks. The integration router may also be configured to automatically connect with each of the plurality of heterogeneous subnetworks. The integration router may then provide persistent network connectivity between user nodes (e.g., electronic devices) across the plurality of heterogeneous subnetworks.

The integration router may automatically connect with each of the plurality of heterogeneous subnetworks without individual manual configuration of parameters associated with each of the plurality of heterogeneous subnetworks. The integration router may provide dynamic route selection between a first electronic device on one of the plurality of heterogeneous subnetworks and a second electronic device on another of the plurality of heterogeneous subnetworks.

The low-overhead routing method may use different IP packets to send/receive data between electronic devices and/or a central hub. For instance, the application may receive an IP packet (having a first IP header and a first IP data field) from a sender device. The IP packet may also contain a final destination corresponding to a destination device communicatively coupled to the routing device via a network route including at least two hops between the routing device and the final destination. The application may then generate a second IP packet having a second IP header and a second IP data field. The second IP data field may be a copy of the first IP data field, and a destination IP address field in the second IP header may include an IP address of a next hop on the network route. The second IP packet may not include an IP address of the final destination in the second IP header. Utilizing these IP packets, the application may transmit data between an electronic device and a central hub (or another electronic device) using these IP packets as described above. Low-overhead routing method is described fully in U.S. application Ser. No. 15/425,364, filed Feb. 6, 2017, which is incorporated herein in its entirety.

In another configuration, the application may utilize various NFC protocols to transfer data. NFC communication protocols may refer to a set of protocols that enables electronic devices to establish radio communication with each other by touching the devices together or bringing them into a predetermined proximity (e.g., a predetermined distance).

In a non-limiting example, users operating the electronic devices may "bump" electronic device (e.g., bring the electronic devices within a close proximity) to transfer data. When the application identifies two electronic devices are within close proximity, the application transmits data between the electronic devices. The application may transmit data from the first electronic device to the second device and vice versa. As described above, the application may ensure that all electronic devices store data from all other electronic devices. In this way, one or more electronic devices may act as a "data magnet."

In some embodiments, the electronic devices may transfer data to a central hub. One or more users may send/receive medical to/from a central hub by "bumping" their electronic devices with the hub. For instance, medic operating mobile devices may first input data then "bump" their mobile device with a central electronic device acting a hub for all medics to send/receive data. The hub may receive new medical data from each electronic device and may also transmit medical data received from other electronic devices operated by other users/medics.

In some embodiments, the application may utilize a Crypto-Partitioning Aware Protocol adapter for Tactical Networks (CAPTAIN) method to send/receive data between the electronic devices and/or the central hub. The CAPTAIN method may provide communication between devices in different networks where the communication must first pass through an encryption mechanism and the devices do not have the stand-alone capability to encrypt or decrypt the communication. According to these techniques, an adapter (e.g., the application executing on the sender electronic device) may determine certain fields in a data packet that remain unencrypted when the data packet passes through the encryption mechanism. The adapter may then process those fields in such a way that, when the data packets are received by a second adapter, the second adapter (e.g., the application executing on the receiver electronic device) may read those fields and obtain the medical data. The CAPTAIN data routing method is described fully in U.S. Pat. No. 9,191,377, which is incorporated herein in its entirety.

In another configuration, the application may enable packet replication routing with destination address swap communication protocols described in U.S. application Ser. No. 15/593,883. The application may utilize a wired communication between one or more electronic devices and/or the hub. In order to minimize the risk of data compromise, the electronic devices may use a wired conventions to other electronic devices and/or a central hub.

The application may utilize one or more of the "offline communication" methods described above to send/receive data from one or more electronic devices to one or more other electronic devices and/or the central hub.

At step 220, the application may receive a request from a server associated with the database of a secondary medical unit requesting the second software application to transmit at least a part of medical data associated with at least one user.

The application may receive a request from a server of (or otherwise associated with) the secondary medical unit to transmit the medical data. As described above, the secondary medical unit may request medical data to further analyze the medical data. The secondary medical unit may also refer to an evacuation unit transferring the wounded. Therefore, it may be imperative for the personnel of the secondary evacuation unit to review the medical data inputted by the primary medical unit (e.g., medical professionals inputting medical data using the first application).

At step 230, the application may in response to authenticating the request, transmit the medical data transmit associated with the first software application of the predetermined number of other electronic devices within the plurality of electronic devices to the database.

The application may first authenticate the request to ensure its legitimacy. The application may execute various authentication and verification methods to identify whether the request is received from a trusted source (e.g., secondary medical unit). If the application positively authenticate the request, the application enables various communication protocols between one or more electronic devices (and/or the central hub) with the secondary medical unit (e.g., a server associated with the secondary medical unit).

In some embodiments, the application may enable online communication between a server/database of the secondary evacuation unit and other electronic devices and/or the central hub. Additionally or alternatively, the application may enable the online communication for a predetermined period of time. In some configurations, the application may automatically enable online communication when the application determines that the secondary medical unit is within a predetermined proximity to one or more of the electronic devices and/or the central hub. In some embodiments, the application may communicate with the secondary medical unit using various offline communication methods described above.

Non-Limiting Example

Figure 3:
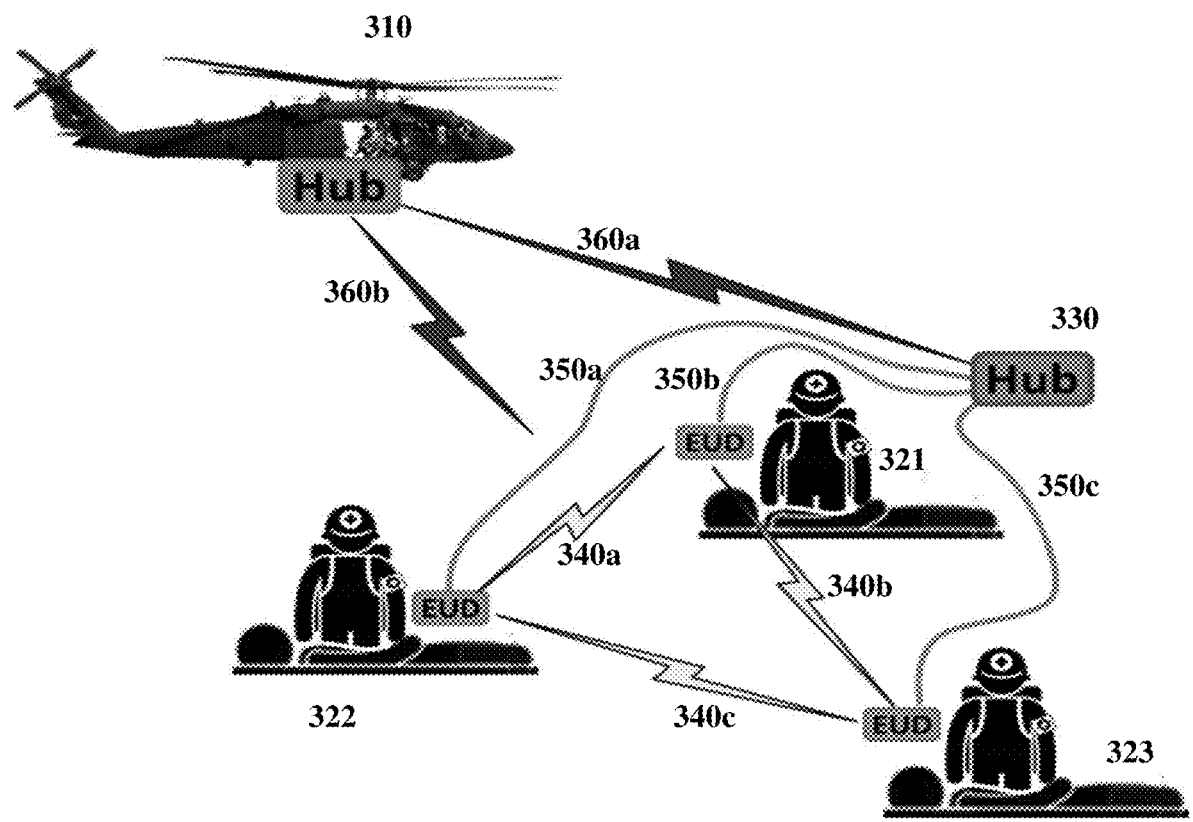
FIG. 3 illustrates a non-limiting example of sharing medical data in a DIL environment, according to an embodiment.

As depicted in FIG. 3, three first responders treat three wounded soldiers. Each first responder may operate an emergency unit device (EUD), such as EUD 321-323. Each EUD may comprise at least two applications. The first application may be a medical application configured to receive triage information and other medical data associated with the wounded soldiers. The second application may be an application that enables secure communication between the EDUs and the HUB 330 and/or the medical evacuation unit 310. For clarity, the second application is also referred to in this non-limiting example as the communication application.

The communication application may identify that the EUDs are operating within a DIL environment. As a result, the communication application may allow offline communication between EUDs (communication 340a-c). In order to transmit/receive data, the first responders may have to bring the EUDs within a predetermined proximity to each other (e.g., bump EUDs).

Additionally or alternatively, the communication application may allow offline communication among the EUDs and the hub 330. Each time any EUD communicates with the hub 330, the communication application transmits medical data stored onto other EUDs to the Hub 330. For instance, when the EUD 322 bumps EUD 323, the communication application executing on these EUDs transfers medical data of the EUD 322 to the EUD 323 and vice versa. Subsequently, when EUD 321 bumps EUD 323, the second application executing on these EUDs transfers the medical data of the EUD 323 and EUD 322 to the EUD 321 and vice versa. As a result, when any of the EUDs bump with the hub 330, the communication application transfers all the data (e.g., medical data of the EUD 321-323) to the hub 330. In some configurations, the hub 330 may also transfer data back to EUDs. For instance, if the EUD 321 does not have the medical data stored on the EUD 323, the hub 330 may transmit this data to the EUD 321 when the EUD 321 bumps with the hub 330. In this way, a connection between any of the EUDs or the hub 330 with the medical evacuation unit 310 ensures that the medical evacuation unit 310 has access to all the latest medical data.

The communication application receives a request from a server or a hub of the medical evacuation unit 310 arrives. The request may also include identification information associated with the medical evacuation unit 310. The communication application may first authenticate the request. If a positive authentication is achieved, the communication application may then allow online and/or offline communication protocols between the EUDs and/or the hub 330.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the principles of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

The previous description is of a preferred embodiment for implementing the invention, and the scope of the invention should not necessarily be limited by this description. The scope of the present invention is instead defined by the following claims.

What is claimed is:

1. A computer system for enabling communication in disrupted communication networks, the computer system comprising:
    a database associated with a medical evacuation vehicle and configured to store medical data associated with one or more users from at least one electronic device;
    a plurality of electronic devices, each electronic device having:
        a first software application configured to receive medical data associated with one or more users; and
        a second software application configured to enable communication of at least one other electronic device within the plurality of electronic devices and the database, the second software application further configured to:
            in response to detecting a disruption within a communication network among the plurality of electric devices, executing an offline communication protocol to transmit and synchronize the medical data associated with the first software application to a predetermined number of other electronic devices within the plurality of electronic devices, wherein the offline communication protocol does not use the communication network;
            receive a request from a server associated with the database to transmit at least a part of the medical data associated with at least one user; and
            in response to authenticating the request, transmit and synchronize the at least a part of the medical data associated with the first software application of the predetermined number of other electronic devices within the plurality of electronic devices to the database.

2. The computer system of claim 1, wherein the predetermined number of other electronic devices corresponds to all other electronic devices within the plurality of electronic devices.

3. The computer system of claim 1, wherein the offline communication protocol is a near field communication protocol.

4. The computer system of claim 3, wherein the near field communication protocol is configured to transmit data from a first electronic device to a second electronic device.

5. The computer system of claim 3, wherein the near field communication protocol is configured to transmit data from any electronic device to a hub communication device.

6. The computer system of claim 5, wherein the hub communication device is configured to store medical data received from one or more electronic devices and transmit all the medical data stored to at least one electronic device within the plurality of electronic devices.

7. The computer system of claim 1, wherein the offline communication protocol is transmitting data using an encrypted media element.

8. The computer system of claim 1, wherein the second software application is configured to:
    disable online communication associated with the plurality of electronic devices in response to detecting a disruption within a communication network among the plurality of electric devices, executing an offline communication protocol.

9. The computer system of claim 8, wherein online communication comprises at least one of radio frequency communication and Wi-Fi communication.

10. The computer system of claim 8, wherein the second software application is configured to:
    enable online communication associated with the plurality of electronic devices when one or more predetermined events are detected.

11. A computer-implemented method for enabling communication in disrupted communication networks, the method comprising:
    in response to detecting a disruption within a communication network among a plurality of electronic devices, executing, by a first application executing on at least one electronic device, an offline communication protocol to transmit and synchronize medical data to a predetermined number of other electronic devices within the plurality of electronic devices, wherein the offline communication protocol does not use the communication network, and wherein the medical data is inputted by a user operating an electronic device via a second application executing on the plurality of electronic devices;
    receiving, by the second application, a request from a server associated with a database of a medical evacuation vehicle to transmit at least a part of the medical data associated with at least one user; and
    in response to authenticating the request, transmitting and synchronizing, by the second application, the medical data associated with the first application of the predetermined number of other electronic devices within the plurality of electronic devices to the database.

12. The method of claim 11, wherein the predetermined number of other electronic devices corresponds to all other electronic devices within the plurality of electronic devices.

13. The method of claim 11, wherein the offline communication protocol is a near field communication protocol.

14. The method of claim 13, wherein the near field communication protocol is configured to transmit data from a first electronic device to a second electronic device.

15. The method of claim 13, wherein the near field communication protocol is configured to transmit data from any electronic device to a hub communication device.

16. The method of claim 15, wherein the hub communication device is configured to store medical data received from one or more electronic devices and transmit all the medical data stored to at least one electronic device within the plurality of electronic devices.

17. The method of claim 11, wherein the offline communication protocol is transmitting data using an encrypted media element.

18. The method of claim 11, further comprising:
disabling, by the application, online communication associated with the plurality of electronic devices in response to detecting a disruption within a communication network among the plurality of electric devices, executing an offline communication protocol.

19. The method of claim 18, wherein online communication comprises at least one of radio frequency communication and Wi-Fi communication.

20. The method of claim 18, further comprising:
enabling, by the application, online communication associated with the plurality of electronic devices when one or more predetermined events are detected.

* * * * *